United States Patent [19]

Duraffourd et al.

[11] Patent Number: 4,668,516

[45] Date of Patent: May 26, 1987

[54] COMPOSITION FOR REGENERATING THE COLLAGEN OF CONNECTIVE SKIN TISSUE AND A PROCESS FOR ITS PREPARATION

[76] Inventors: Alain Duraffourd; Jean-Max Duraffourd, both of 11 bis avenue Victor Hugo, 75116 Paris, France

[21] Appl. No.: 689,050

[22] PCT Filed: Mar. 23, 1984

[86] PCT No.: PCT/FR84/00079

§ 371 Date: Nov. 28, 1984

§ 102(e) Date: Nov. 28, 1984

[87] PCT Pub. No.: WO84/03836

PCT Pub. Date: Oct. 11, 1984

[30] Foreign Application Priority Data

Mar. 30, 1983 [FR] France ............................... 83 05282

[51] Int. Cl.$^4$ ..................... A61K 35/78; A61K 31/35; A61K 31/34
[52] U.S. Cl. ................................ 424/196.1; 514/454; 514/474
[58] Field of Search .......................... 424/196.1, 195.1; 514/474, 454

[56] References Cited

FOREIGN PATENT DOCUMENTS 855118 6/1977 Belgium .
2191878 2/1974 France .
2249651 5/1975 France .
2275193 1/1976 France .

OTHER PUBLICATIONS

Stone, I. Healing Factor, Vitamin C Against Disease, 1974, Grosset and Dunlap, pp. 47 & 48.
"The Merck Index", Tenth Edition, p. 174, No. 1226, Ref. 1226, Quercitrin, Merck & Co., Inc. Rahway, N.J., 1983.
"Effect of Flavonols on Ascorbic Acid and Anthocyanintability in Model Systems", *Chemical Abstracts*, vol. 82, No. 13, Mar. 31, 1975, Colombus, Ohio, p. 389.

Primary Examiner—Johnnie R. Brown
Assistant Examiner—John W. Rollins
Attorney, Agent, or Firm—Young & Thompson

[57] ABSTRACT

A composition for regenerating the collagen of the connective tissue of the skin contains an aqueous conifer bark extract buffered to a pH of about 7, water-soluble flavonols and vitamin C. It is particularly useful for treating wrinkles.

5 Claims, No Drawings

COMPOSITION FOR REGENERATING THE COLLAGEN OF CONNECTIVE SKIN TISSUE AND A PROCESS FOR ITS PREPARATION

This invention relates to a composition for regenerating the collagen of connective skin tissue.

Collagen is the main constituent (70% of the connective tissue) making up the supporting tissue of the organs, and particularly the skin.

Collagen consists of long elastic polypeptide fibres interconnected by bridges which provide the cohesion and stability of the connective tissue. This texture enables it to act as an elastic tissue in every direction and retain water, thus actively taking part in water control at the skin. Collagen ageing manifests itself as a break in the connections between the fibres. Age, severe weather, and pollution accelerate these breaks and slow down their renewal. Accordingly, the skin loses its elasticity and dehydrates. The resulting slackening of the skin causes ugly wrinkles and the like to form.

These disadvantages are not only concerned with aesthetics. The skin is not just a covering; it is an organ which has numerous properties which are essential to proper operation of the entire organism. For this purpose the skin has a highly developed vascular system which underlies exchanges which are essential to the performance of the various skin functions. The walls of the capillaries of this vascular system consist essentially of connective tissue. Its deterioration reduces the elasticity of the walls, thus modifying the pressure ratios between the arterial part and the venous part, which underlie the mechanism responsible for the arterial flow and the venous return, hence nutrition of the skin and the specific metabolisms of its activity.

Irrespective of the disorders that may result from the slowing down of the various skin functions, skin malnutrition is manifested by ageing of the skin, resulting from inadequate renewal of the old cells.

It is therefore doubly important to correct these functional deficiencies of the skin, since this affects physical health by renewing the physiological activity of the skin and it also affects mental health because of the aesthetic appearance of such correction.

The object of this invention is to provide a solution to the problem indicated hereinabove.

According to the invention, the composition for regenerating the collagen of the connective tissue of the skin, is characterised in that it contains an aqueous conifer bark extract buffered to a pH of about 7 containing water-soluble flavonols and vitamin C.

The flavonols extracted from the barks of conifers such as pine and cypress, have the following formula

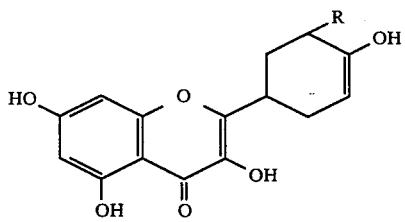

wherein R denotes a lower alkyl radical.

Applicant has surprisingly found that these flavonols have a positive action on regeneration of the collagen of the connective tissue.

It has also been found that the presence of vitamin C in the aqueous extract not only provides the organism with vitamin C but also potentiates the effects of the flavonols.

Flavonols extracted from conifer barks tend to polymerise readily thus losing their activity on collagen regeneration.

The presence of the buffer to give a pH of about 7 in the composition obviates this polymerization and enables the flavonols to be kept in solution, more particularly in the form of dimers, which are the most active.

Experiments carried out on animals have shown that the composition according to the invention diffuses perfectly into the skin and readily reaches not only the connective skin tissue but also the connective vascular tissue. Local application of the composition according to the invention is therefore perfectly suitable for the treatment of connective tissue deficiencies, giving a specific and complete correction thereof.

According to another aspect of the invention, the process for the preparation of the composition according to the invention comprises the following steps:

(a) Confier barks are infused with boiling and then macerated in water to which alcohol has been added, (b) The resulting suspension if filtered and a natural anti-oxidant is added and a buffer is added to keep the pH at a value of about 7, (c) Conifer needles are macerated in water to which a buffer has been added to keep the pH at a value of about 7, and then the solution is filtered and (d) The resulting filtrate is mixed with the filtrate obtained at the end of step (b).

With this procedure appreciable quantities of flavonols are extracted while at the same time their polymerization is obviated.

Also, step (c) gives a solution which is rich in vitamin C and which enables this vitamin to be added to the flavonol-containing solution obtained in step (b).

Preferably, borate is used as buffer.

Preferably, ethyl gallate is used as anti-oxidant, since this has the advantage of being natural and compatible with the other ingredients of the composition and acceptable by the skin and the connective tissue.

The procedure for the preparation of a composition according to the invention will be given hereinafter by way of example without any limiting force.

An infusion of maritime pine bark was prepared in the proportion of 100 g of crushed bark per 1 liter of water, to which 50 ml of ethyl alcohol was added at 95°.

This infusion was kept at boiling for 20 minutes. The infusion was then followed by maceration for 2 hours in the same alcohol-containing water.

The resulting suspension was then filtered and a natural anti-oxidant added, e.g. ethyl gallate, and a borate buffer to give a pH of 7. This precaution is essential to obviate polymerization of the flavonols by acidification or their oxidation, which would change their properties.

Also, 100 g of dry maritime pine needles were macerated in 1 liter of water, buffered to pH 7, for 2 hours. The resulting suspension was filtered. The recovered filtrate was then mixed with the previous filtrate. Maceration of the pine needles complements not only the active principles (flavonols) but also the vitamin C, which catalyzes the action of the flavonols. The flavonols contained in the resulting solution are analyzed by means of a standard phototungstic reagent. The final strength is adjusted by dilution to give a constant activity.

For its use, the composition obtained above is diluted so as to contain between 1 and 5 g per liter of flavonols and 10 to 50 mg per liter of vitamin C.

Preferably, the composition contains 2.5 g per liter of flavonols and 25 mg per liter of vitamin C.

The composition according to the invention may be aplied to the skin in the form of lotions, creams, ointments, etc.

Some examples of cosmetic formulations of the composition according to the invention are given below.

(1) Lotion:
Standard flavonol solution containing 2.5 g per liter buffered to a pH of 7 and containing an anti-oxidant:
400 ml
Sodium ricinoleate: 10 ml
Hygroplex: 5 ml
Distilled witch hazel to make up to 1000 ml Hypoallergenic perfume: qs (2) Cream:
Standard flavonol solution containing 2.5 g per liter buffered to a pH of 7 and containing an anti-oxidant:
1000 ml
Almond oil: 20 ml
Perhydrosqualene: 3 ml
Emulsifier: 20 g
Distilled rose water to make up to 250 g
Hypoallergenic perfume: qs.

Clinical tests have shown the efficacy of the composition according to the invention in skin applications.

The effective regenerating action of this composition in respect of connective skin tissue collagen enables wrinkles in particular to be effectively treated.

More particularly, the application of the composition according to the invention eliminates wrinkles appearing between the two breasts following the wearing of brassieres in women over the age of 50.

Also, the composition according to the invention has an effective action in the local treatment of varices and hemorrhoids. The composition according to the invention may also be administered by subcutaneous injection. One example of the formulation of an injectable ampoule is given below:
Standard flavonol solution containing 2.5 g per liter buffered to a pH of 7 and containing an anti-oxidant:
10 ml.

We claim:

1. A composition for regenerating the collagen of the connective tissue of the skin, containing an aqueous extract of at least one member selected from the group consisting of bark and needles of pine and cypress, said extract containing buffer in an amount sufficient to maintain the pH of said extract at about 7, water-soluble flavonols in the form of dimers and vitamin C in an amount of about 10 mg per gram of flavonols, said composition having between 1 and 5 g per liter of said flavonols.

2. A composition according to claim 1, containing a borate-based buffer and a natural anti-oxidant compatible with the other ingredients of the composition and acceptable by the skin.

3. A process for the preparation of a composition for regenerating the collagen of the connective tissue of the skin, comprising the following steps:
(a) infusing pine bark with boiling water for about twenty minutes in the proportion of about 100 g bark per liter water, and then macerating said bark in water for about two hours to which alcohol has been added in a proportion of about 50 ml alcolol per liter water,
(b) filtering the resulting suspension and adding an anti-oxidant and a buffer in an amount sufficient to keep the pH at a value of about 7,
(c) macerating pine needles in water, in a proportion of about 100 g needles per liter water to which a buffer has been added in an amount sufficient to keep the pH at a value of about 7, and then filtering the solution, and
(d) mixing the resulting filtrate with the filtrate obtained at the end of step (b).

4. A process according to claim 3, wherein a borate is used as said buffer.

5. A process according to claim 3, wherein ethyl gallate is used as said anti-oxidant.

* * * * *